United States Patent
Benicewicz et al.

(10) Patent No.: US 7,440,097 B2
(45) Date of Patent: Oct. 21, 2008

(54) LASER PLASMA SPECTROSCOPY APPARATUS AND METHOD FOR IN SITU DEPTH PROFILING

(75) Inventors: Pamela King Benicewicz, Loudonville, NY (US); Pavel Alexeyevich Fomitchov, New York, NY (US); Elena Rozier, Schenectady, NY (US); John Ruediger Mader Viertl, Niskayuna, NY (US); Tymm Bradner Schumaker, Saratoga Springs, NY (US)

(73) Assignee: General Electric Company, Niskayuna, NY (US)

( * ) Notice: Subject to any disclaimer, the term of this patent is extended or adjusted under 35 U.S.C. 154(b) by 113 days.

(21) Appl. No.: 11/426,708

(22) Filed: Jun. 27, 2006

(65) Prior Publication Data

US 2007/0296966 A1 Dec. 27, 2007

(51) Int. Cl.
*G01J 3/443* (2006.01)
*G01J 3/30* (2006.01)
*G01N 21/63* (2006.01)
*G01B 11/22* (2006.01)
*G01B 11/06* (2006.01)

(52) U.S. Cl. .......... 356/316; 356/318; 356/626
(58) Field of Classification Search .......... 356/316, 356/318, 626
See application file for complete search history.

(56) References Cited

U.S. PATENT DOCUMENTS

| | | | | |
|---|---|---|---|---|
| 4,645,342 | A | * | 2/1987 | Tanimoto et al. ........... 356/318 |
| 5,583,634 | A | * | 12/1996 | Andre et al. ............... 356/318 |
| 5,751,416 | A | * | 5/1998 | Singh et al. ............... 356/311 |
| 5,798,832 | A | * | 8/1998 | Hnilica et al. ............. 356/316 |
| 5,847,825 | A | * | 12/1998 | Alexander ................. 356/318 |
| 6,008,897 | A | | 12/1999 | Sabsabi et al. |
| 6,532,068 | B2 | | 3/2003 | Detalle et al. |
| 6,661,511 | B2 | | 12/2003 | Detalle et al. |

(Continued)

FOREIGN PATENT DOCUMENTS

DE   4138157 A1 *   5/1993

(Continued)

OTHER PUBLICATIONS

Cravetchi, I.V.; Taschuk, M.T.; Tsui, Y.Y.; Fedosejevs, R.F.; Evaluation of femtosecond LIBS for spectrochemical microanalysis of alluminum alloys, 2006, Anal. Bioanal. Chem., v.385, p. 287-294.*

(Continued)

*Primary Examiner*—Gregory J Toatley, Jr.
*Assistant Examiner*—Bryan Giglio
(74) *Attorney, Agent, or Firm*—Ann M. Agosti (57) ABSTRACT

An in-situ laser plasma spectroscopy (LPS) system for automated near real-time elemental depth profiling of a target including: an optical source configured to generate an optical beam, wherein the optical beam is pulsed; an optical probe system configured to deliver the optical beam from the optical source to a surface of a target to generate an ablation plasma; a time resolved spectral detection system configured to generate time resolved spectral data from emission signals from the ablation plasma; and a data acquisition and processing system configured to acquire the time resolved spectral data to determine, in combination with predetermined calibration data, an absolute elemental concentration as a function of depth in near real-time.

37 Claims, 9 Drawing Sheets

U.S. PATENT DOCUMENTS

| | | | |
|---|---|---|---|
| 6,762,836 B2* | 7/2004 | Benicewicz et al. | 356/318 |
| 6,873,419 B2 | 3/2005 | Detalle et al. | |
| 7,064,825 B2 | 6/2006 | Viertl et al. | |
| 7,251,022 B2* | 7/2007 | Martin et al. | 356/72 |
| 2004/0102764 A1* | 5/2004 | Balling | 606/5 |
| 2005/0068524 A1 | 3/2005 | Wu et al. | |
| 2006/0262302 A1* | 11/2006 | Eklin | 356/318 |
| 2007/0265783 A1* | 11/2007 | Mound | 702/8 |

FOREIGN PATENT DOCUMENTS

EP    1068516    5/2003

OTHER PUBLICATIONS

Pasquini, C; Cortez, J.; Silva, L.M.C; Gonzaga, F.B., Laser Induced Breakdown Spectroscopy, 2007, J. Braz. Chem., v.18, n.3, p. 463-512.*

Papazoglou, D.G.; Papadakis, V.; Anglos, D; In situ interferometric depth and topography monitoring in LIBS elemental profiling of multi-layer structures, 2004, J. Anal. At. Spectrom., v.19, p. 483-488.*

Kanicky, V.; Otruba, V.; Depth profiling of tin-coated glass by laser ablation inductively coupled plasma emission spectrometry with acoustic signal measurement, Fresenius J. Anal. Chem., 2000, v.366, p. 288-233.*

Balzer, H.; Hoehne, M.; Sturm, V.; Noll, R; Online coating thickness measurement and depth profiling of zinc coated sheet steel by laser-induced breakdown spectroscopy, 2005, Spectrochimica Acta Part B, v.60, p. 1172-1178.*

Mateo, M.P.; Vadillo, J.M.; Laserna, J.J.; Irradiance-dependent depth profiling of layered materials using laser-induced plasma spectrometry, 2001, J. Anal. At. Spectrom. v.16, p. 1317-1321.*

Anderson, D.R.; McLeod, C.W.; English, T.; Smith, T.A.; Depth Profile Studies Using Laser-Induced Plasma Emission Spectrometry, 1995 J. Applied Spectroscopy, v.49, n.6.*

Jose M. Vadillo and J. J. Laserna; "Depth-resolved Analysis of Multilayered Samples by Laser-induced breakdown Spectrometry"; Journal of Analytical Atomic Spectrometry, Aug. 1997, vol. 12 (859-862).

* cited by examiner

LASER PLASMA SPECTROSCOPY APPARATUS AND METHOD FOR IN SITU DEPTH PROFILING

BACKGROUND

The invention relates generally to depth profiling and more particularly to depth profiling using laser plasma spectroscopy.

Exposure to high temperatures for extended periods of time can damage metal parts of machinery such as buckets, blades, and nozzles in turbine engines. In gas turbine engines, such damage can result in a reduction in airflow and thus efficiency. Damage to blades can eventually lead to failure of the engine. Coatings are frequently used to protect metal parts such as turbine blades from the effects of high temperature exposure for extended time periods that can damage the blades and reduce lifetime. Although the coatings extend the lifetime of the metal components, the coatings themselves are affected by this exposure over time.

Currently, all the buckets, blades, and nozzles are stripped and recoated after a given exposure interval, or the engine is partially disassembled and a sample part is removed and sacrificed for analysis. Both procedures result in lengthy outage times. However, it has been recognized that lifetime of the coatings can be predicted by the concentration of various elements in the coating as a function of depth. Although a number of analytical techniques exist for measuring elemental concentration as a function of depth, they all either invoke destructive analysis of the part or substrate (e.g., secondary ion mass spectroscopy and electron microprobe analysis) or cannot be performed remotely or in situ (e.g., laser ablation mass spectroscopy), especially in real time.

Therefore there is a need for an in situ and near real-time analysis technique for depth profiling, which is nondestructive to the substrate and which removes the need for disassembling the machinery.

BRIEF DESCRIPTION

One embodiment of the present invention is an in-situ laser plasma spectroscopy (LPS) system for automated near real-time elemental depth profiling of a target including an optical source configured to generate an optical beam, wherein the optical beam is pulsed, an optical probe system configured to deliver the optical beam from the optical source to a surface of a target to generate an ablation plasma, a time resolved spectral detection system configured to generate time resolved spectral data from emission signals from the ablation plasma, and a data acquisition and processing system configured to acquire the time resolved spectral data to determine, in combination with predetermined calibration data, an absolute elemental concentration of the target as a function of depth in near real-time.

Another embodiment of the present invention is an in-situ, portable laser plasma spectroscopy system for automated near real-time elemental depth profiling of a coating, including an optical source configured to generate an optical beam, wherein the optical beam is pulsed, an optical probe system configured to deliver the optical beam from the optical source to a coating surface on a target substrate to generate an ablation plasma, wherein the optical probe system comprises a beam-shaping element to produce an optical illumination zone of substantially uniform optical energy through a thickness of the coating, a time resolved spectral detection system configured to generate time resolved spectral data from emission signals from the ablation plasma, and a data acquisition and processing system configured to acquire the time resolved spectral data and to acquire calibration data prior to acquisition of time resolved spectral data to determine an absolute elemental concentration of the coating as a function of depth in near real-time.

In still another embodiment of the present invention is a method for in-situ, near real time depth profiling, including (a) acquiring calibration data, (b) performing at least one ablation cycle including generating an optical beam, wherein the optical beam is pulsed, homogenizing the intensity of the optical beam to produce an optical illumination zone of substantially uniform optical energy on a surface of the target, and delivering the optical beam at the surface of the coating to generate an ablation plasma, (c) generating time resolved spectral data from emission signals received from the ablation plasma, and (d) determining absolute elemental concentration at the probed surface of the target in near real-time.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Embodiments of the present invention relate to laser plasma spectroscopy systems and methods for in situ, automated near-real time quantitative analysis of elemental concentration as a function of depth for targets. As used herein, the term "target" may refer to a unitary structure or a structure including a substrate and a coating. The target may be a composite including multiple layers of different materials. When an optical beam of sufficient energy is incident on the target, a portion of the target material is vaporized (ablated), forming a plasma, consisting of excited ionic, atomic, and molecular species of the vaporized material. The nature and characteristics of the ablation plasma depend on various parameters including the chemical composition of the target, wavelength of the radiation, and the energy used to ablate the target material. The composition of the ablation plasma will also depend on its distance from the target surface as a result of the rapid expansion of the ablation plasma from the target followed by the lowering of its temperature. The elemental composition of the material is obtained by analyzing time resolved spectral data. This data is generated by spectrally dispersing the emission signals from the plasma and directing this dispersed light onto photodetectors. The photodetectors are gated (turned on and off for a specified duration) and the gate is delayed with respect to the generation of the plasma so that only specific emissions of interest are captured. Therefore the captured spectral data only corresponds to emission signals emitted at a certain time delay after the generation of the plasma and for a certain duration.

The elemental concentration of the target as a function of depth is evaluated in near real-time using previously acquired calibration data. As used herein, the term "near real-time" refers to a configuration of the system whereby an absolute elemental concentration can be determined substantially immediately after the acquisition of spectral data. Substantially immediately refers to a time period from zero to a time practically required to process the spectral data after acquisition. In one non-limiting example, upon acquisition of spectral data after one ablation cycle corresponding to a depth in a target, the elemental concentration is substantially immediately determined using previously acquired calibration data. In another example, a plurality of spectral data through successive depths is first acquired and the elemental concentration for the various depths of the target is determined substantially immediately after the acquisition of the plurality of spectral data. As used herein, the term "absolute elemental concentration" refers to a concentration value that is determined independently of other elements present in the target and is not a relative measurement.

In one embodiment of the present invention, the laser spectroscopy system includes an optical source configured to generate an optical beam, which is pulsed. In a non-limiting example, the optical source is a laser source with a pulsed output capable of achieving peak intensities of greater than about 1 $GW/cm^2$. In one example, a Nd:YAG laser is used. The fundamental output of the Nd:YAG laser or any of its harmonics may be used for ablating the target.

The laser spectroscopy system further includes an optical probe system including optical elements configured to deliver the optical beam from the optical source to a surface of a target to generate an ablation plasma. In a further embodiment, the optical probe system is further configured to collect and deliver the emission signals from the ablation plasma to a time resolved spectral detection system. Suitable examples of optical elements include optical fibers, dichroic mirrors, lenses, mirrors, beam splitters, filters, and polarizers. In some embodiments, the system includes optical beam-shaping elements to control beam parameters such as beam diameter, beam divergence, size of illumination zone and distribution of optical energy within the illumination zone. In a non-limiting example, the optical probe system includes an intensity-homogenizing element such as a mode scrambler or a non-linear attenuator, to produce an optical illumination zone of substantially uniform optical energy on the surface of the target. As used herein, the term "illumination zone" refers to a zone illuminated by the optical beam on the surface of the target. As used herein, the term "optical illumination zone of substantially uniform optical energy" refers to an illumination zone having 75% of the central area of the illumination zone being illumed by optical energy uniform to within plus or minus 5% of the average energy of illumination with the optical energy dropping at the outer region of the illumination zone. Other beam-shaping elements include collimating elements to produce a collimated beam. In a non-limiting example, the collimating element includes a positive lens and a negative lens combination, which is collimated over a length comparable to the thickness being interrogated.

The time resolved spectral detection system including a spectrometer and a photodetector generates time resolved spectral data from the emission signals. The system further includes a data acquisition and processing system automated to acquire the time resolved spectral data. Calibration data for analysis is previously determined and acquired by the data acquisition and processing system. As used herein, calibration data includes elemental spectral intensity calibration data and depth calibration data. The data acquisition and processing system on acquisition of spectral data is capable of substantially immediate determination of absolute elemental concentration at the probed surface of the target using predetermined calibration data.

Figure 1:
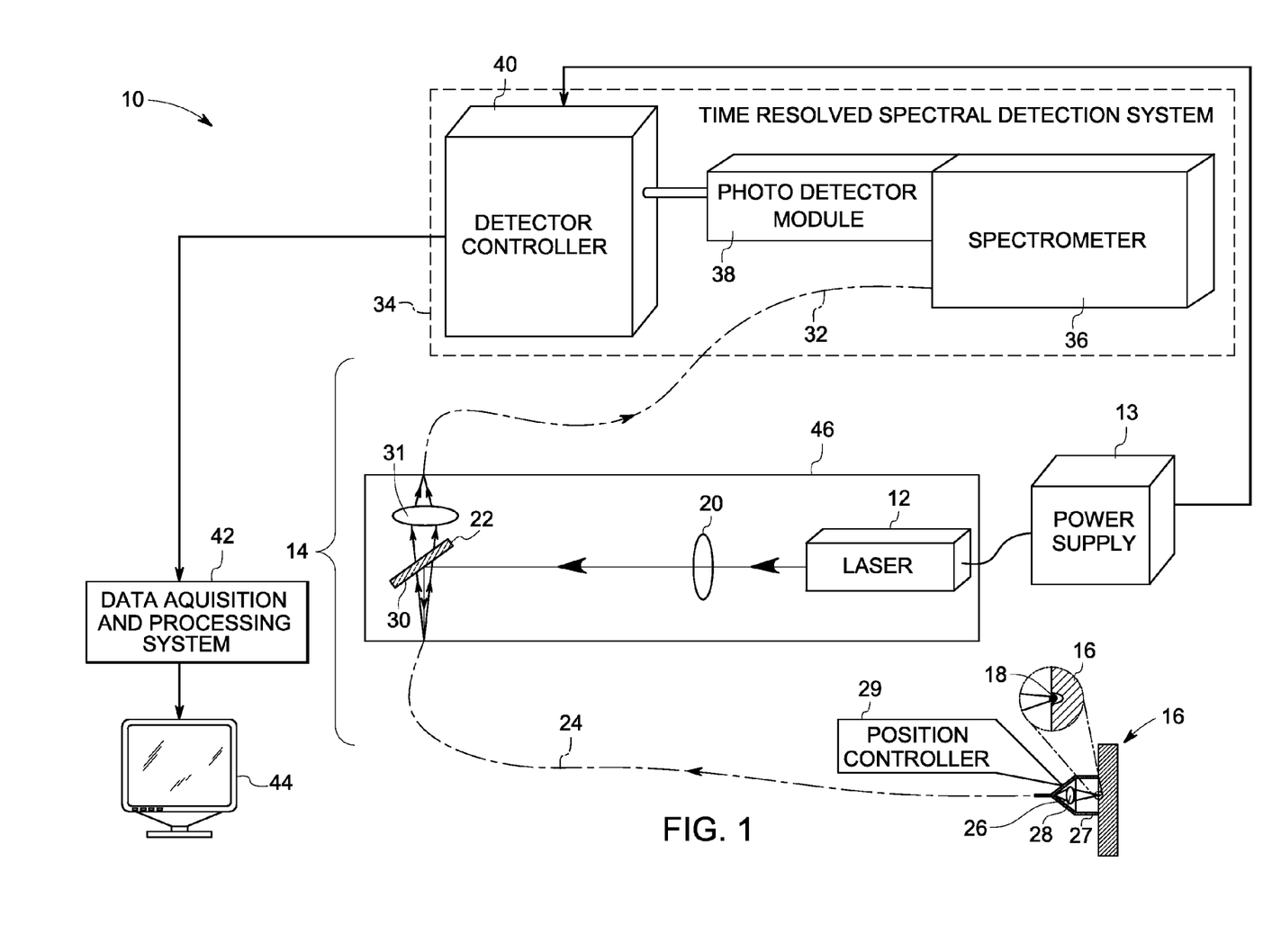
FIG. 1 is a schematic representation of a laser plasma spectroscopy system in one embodiment of the present invention.

One embodiment of the present invention is a laser plasma spectroscopy (LPS) system 10 including an optical source 12, a pulsed laser source, for elemental depth profiling of a target 16 as shown in FIG. 1. The laser source 12 is connected to a power supply 13. An optical probe system 14 includes a first fiber coupling lens 20 for coupling a pulsed laser beam from the laser source into an optical pulse delivery fiber 24. A spectral separation element 22, such as a dichroic mirror, reflects the laser beam and couples the beam into the optical pulse delivery fiber 24. The optical pulse delivery fiber 24 ends at a probe head 26 including a probe lens 28 for focusing the laser beam emerging from the fiber onto the target 16.

In some embodiments, alignment fixture 27, such as but not limited to a sheath, is used to encase a part of the optical pulse delivery fiber 24 and the probe lens 28. The alignment fixture provides for a desired alignment of the probe head with respect to the target to provide a desired illumination zone for ablation. In one example, the sheath extends beyond the probe lens 28 by a length substantially equal to the focal distance of the probe lens 28. A fixed focal distance is maintained when the sheath is in contact with the target and provides for focused, substantially normal, within plus or minus 5% off normal, incidence of the laser beam on the target.

In certain embodiments, the optical probe system also includes a position controller 29 to dynamically adjust a distance between the probe-head 26 or probe head element such as the probe lens 28 and the surface of the target between successive ablation cycles. As the target is ablated in successive ablation cycles, and depth of the ablation crater is successively increased, the position controller dynamically repositions the probe head or probe head elements.

When an optical pulse of sufficient intensity hits the target 16, the coating material in a focal volume is vaporized, forming high-temperature plasma 18. As the plasma 18 expands and cools, the plasma emits radiation (emission signal). This emission signal is collected by the probe lens 28, and is imaged onto the optical pulse delivery fiber 24. Upon exiting the optical pulse delivery fiber 24, the emission signal is incident on the dichroic mirror 22. The dichroic mirror 22 is configured to reflect light at the wavelength of the laser beam, but transmit light at wavelengths emitted by the ablation plasma. In one example, if a 1064 nm laser source is used to ablate the target, the laser side 30 of the dichroic mirror is configured to reflect at 1064 nm.

A second fiber coupling lens 31 focuses the emission signal transmitted through the dichroic mirror 22 and couples the beam into an emission signal delivery fiber 32. As used herein and throughout the specification, the term "fiber" refers to a single fiber or alternatively a fiber bundle. The emission signal is carried through the emission signal delivery fiber 32 and is coupled into a time resolved spectral detection system 34 to spectrally and temporally resolve the emissions and to generate time resolved spectral data.

The time resolved spectral detection system 34 includes a spectrometer 36 to spectrally disperse the plasma emission signal. The spectrally dispersed emission signal is then incident on a photodetector module 38. The photodetector module 38 may include, for example, a photodiode array (PDA), a charge coupled device (CCD), a gated charge coupled device, an intensified charge coupled device, and a photomultiplier. In a more specific embodiment, the spectrally dispersed plasma emission signal at various wavelengths is incident on respective photodetectors of the photodetector module 38 to generate the spectral data. Detector controller 40 is used to time gate the photodetector to enable the generation of time resolved spectral data. An electrical or optical trigger may be used to trigger the detector controller 40 to be activated coincident with the generation of the laser pulse. In a non-limiting example, a TTL (transistor-transistor logic) output from the laser corresponding to the start of the ablation cycle, is used to trigger the detector controller 40. The photodetector 38 is then gated by applying high voltage pulses from the detector controller 40 of a specified duration and delay with respect to the generation of the ablation plasma to generate time resolved spectral data. For example, spectral emissions from the plasma may last for hundreds of microseconds after plasma generation. To generate a time resolved spectral data, a time gate (time window) of 10 microseconds or 15 microseconds, for example, after plasma generation is applied to the photodetector to generate data corresponding to emission signals emitted only during a desired time window.

The generated spectral data is sent to data acquisition and processing system 42. The data is analyzed in near real-time using predetermined calibration data. In one embodiment, the predetermined calibration data is present in the data acquisition and processing system 42. The system may further include a display 44 to display the calibrated data.

In some embodiments, part or all of the optical probe system 14 and the optical source 12 are encased in a housing 46. The housing 46 is optionally configured to have standard connectors to which the optical pulse delivery fiber 14 and the emission signal delivery fiber 32 are removably coupled.

Figure 2:
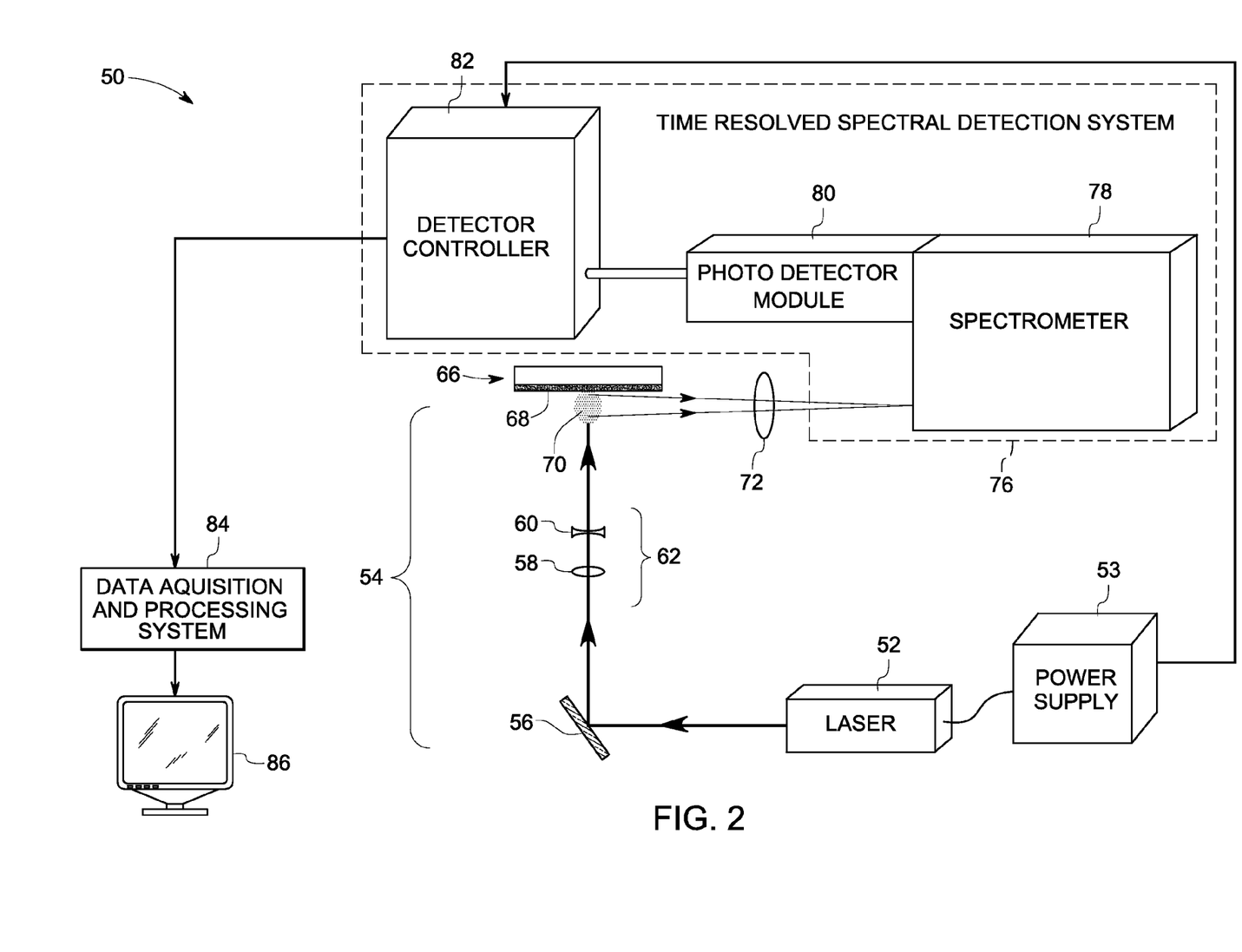
FIG. 2 is a schematic representation of a laser plasma spectroscopy system in another embodiment of the present invention.

Another embodiment of the present invention, as illustrated in FIG. 2, is a laser plasma spectroscopy system 50 including a pulsed laser 52 and an optical probe system 54 in a "free space" configuration without the use of optical fibers. The laser beam from the laser 52 is directed by a mirror 56 through a combination of a positive lens 58 and a negative lens 60, which forms a telescope 62. The telescope 62 acts to collimate and reduce the size of the laser beam. A collimated beam ensures uniform removal of layers in the target at each successive laser pulse. Advantageously with such a telescope, if the beam is collimated over a length at least as long as the coating or desired target sampling thickness, then repositioning the focusing lens as the target is ablated to ensure uniform removal of layers can be avoided. The collimation ensures formation of uniform illumination zone in successive depths of the coating. When the laser beam is incident on target 66 including coating 68, an ablation plasma 70 is formed. This ablation plasma 70 is imaged onto the front entrance slit of the spectrometer using focusing lens 72. The time resolved spectral detection system 76 includes a spectrometer 78 to spectrally disperse the plasma emission signal and a photodetector module 80 to generate time resolved spectral data.

The generated data signal is sent to the data acquisition and processing system 84. The data is analyzed in real time using predetermined calibration data. In one embodiment, the predetermined calibration data is present in a computer readable medium in the data acquisition and processing system. The system further includes a display 86 to display the calibrated data.

Figure 3:
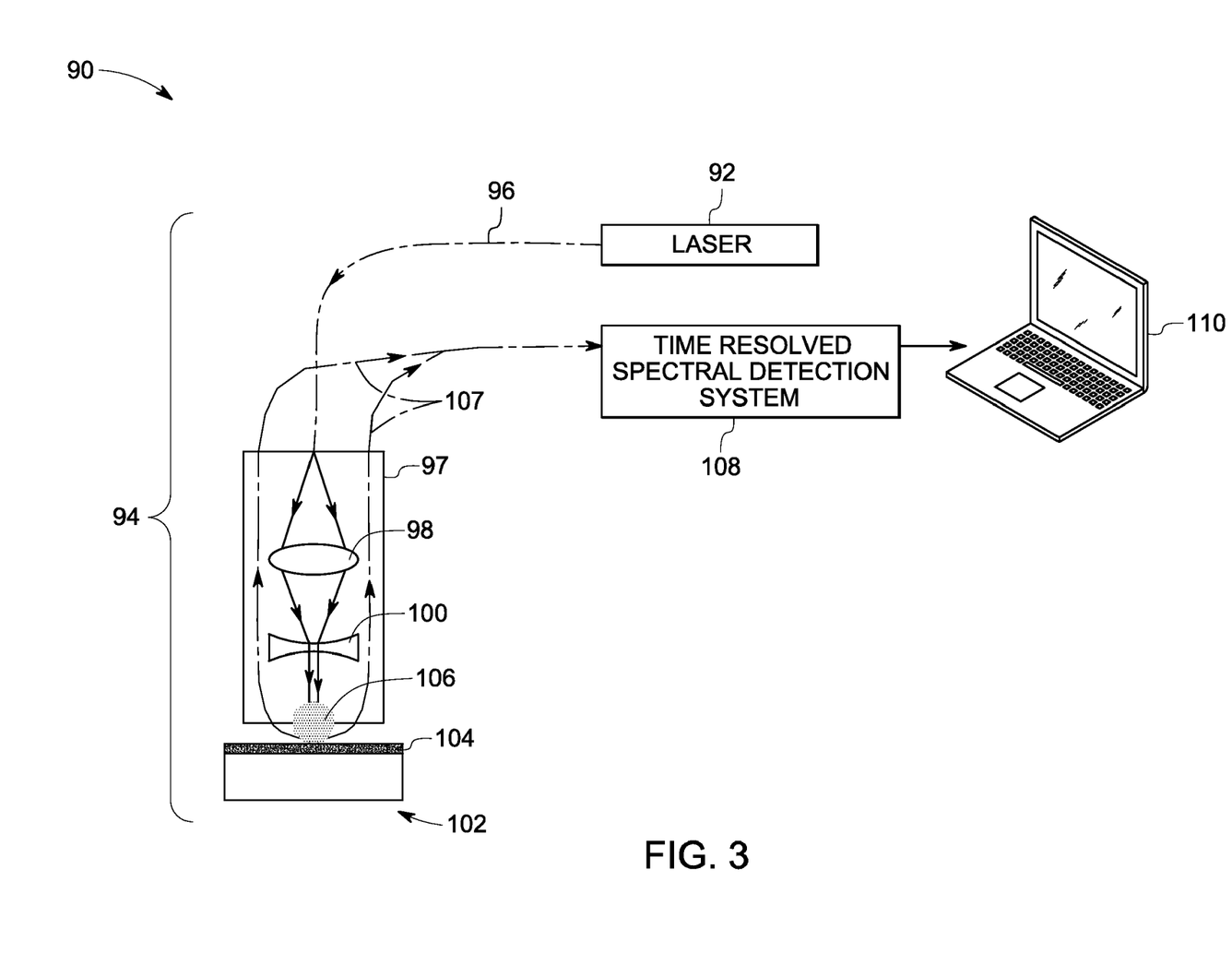
FIG. 3 is a schematic representation of a laser plasma spectroscopy system in still another embodiment of the present invention.

FIG. 3 illustrates another embodiment of the present invention wherein a laser plasma spectroscopy system 90 includes an optical source 92 and an optical probe system 94. A fiber or fiber bundle 96 is used to transmit the optical beam to the combination of lenses 97 including a positive lens 98 and negative lens 100. The optical beam, when incident on the target 102 including a target coating 104, ablates the coating and creates ablation plasma 106.

In one embodiment of the present invention, the laser plasma spectroscopy system is configured for sub-volume sampling of the plasma. This enables sampling of the emission signals selectively from a sub-volume of the plasma. In one embodiment, one or more emission signal delivery fibers or fiber bundles 107 are placed at an angle off normal from the surface of the coating 104. In this embodiment, the transmission of the laser beam to the target and the transmission of the plasma emission signal to the time resolved spectral detection system 108 is achieved using separate optical fibers or fiber bundles. This approach allows for design and optimization of plasma emission signal collection independent of the laser beam delivery to the coating. In one embodiment, a portable data acquisition and processing system such as a laptop 110 is used to collect and analyze data.

Figure 4:
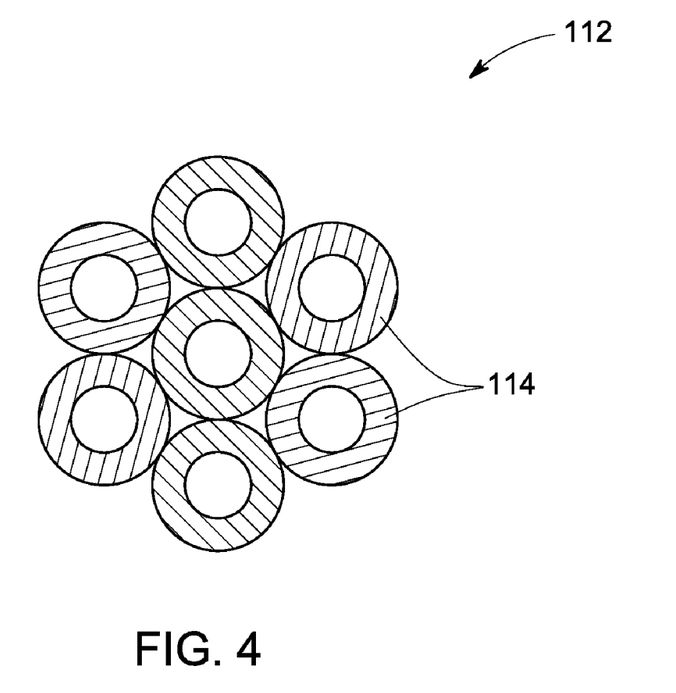
FIG. 4 is a cross-sectional representation of a fiber bundle with linearly arranged fibers at a first end of the bundle in one embodiment of the present invention.
Figure 5:
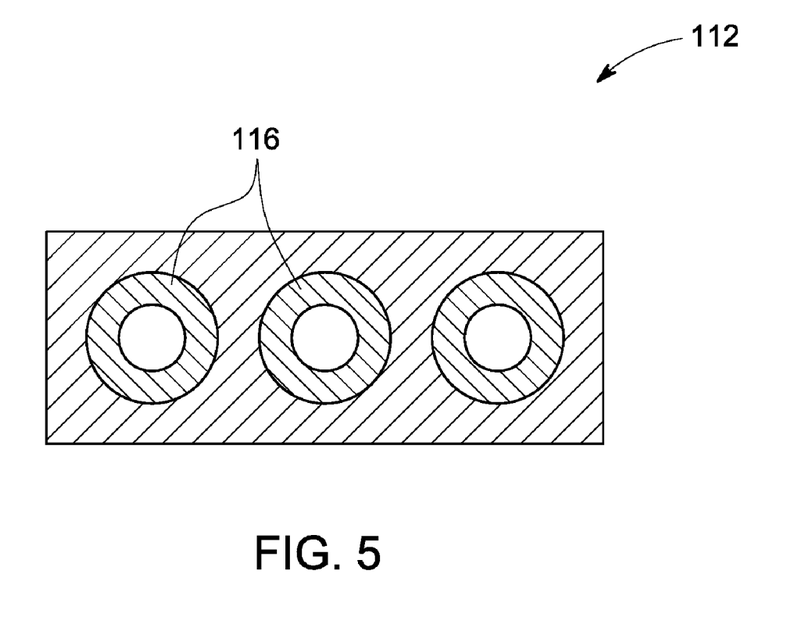
FIG. 5 is a cross-sectional representation of a fiber bundle with linearly arranged fibers at a second end of the bundle in one embodiment of the present invention.

In an embodiment using fiber bundles for collection and delivery of emissions signals, the fibers in the bundle may be desirably arranged to facilitate efficient coupling of emission signals from the plasma into the fiber bundle or from the fiber bundle into a spectrometer. In one embodiment the fibers in the bundle at the plasma end 112 of are arranged compactly to efficiently collect the emission signals from the plasma. As shown in FIG. 4, the fibers 114 at the plasma end of the fiber bundle are arranged hexagonally. As shown in FIG. 5, the same fibers 114 at a spectrometer end 116 of the fiber bundle are arranged linearly to efficiently couple the emission signals out of the fiber bundle and into the spectrometer through the spectrometer slit openings.

In one embodiment, the in-situ laser plasma spectroscopy system for near real-time elemental depth profiling is a portable system. For example, different sub systems such as the optical source, the optical probe system, and the detector spectrometer system are designed to be individually portable and can be removably coupled to each other. Alternatively, all components can be pre-assembled in a portable case or any of a number of movable containers or tables. In a further embodiment, wherein the optical beam and the plasma emission signal are transmitted by optical fibers, the optical source and the time resolved spectral detection system, detector controller and all system components other than the fiber optic probe are remote from the target area.

Another embodiment of the present invention is a method for in-situ, near real time depth profiling. The method includes predetermining the calibration data. Calibration data includes both elemental spectral intensity calibration data and depth calibration data. In a non-limiting example, spectral intensity calibration data is determined by using a calibration target with known elemental concentrations. Those skilled in the art will realize that there are a variety of analytical techniques that may be used for establishing a calibration, including electron microprobe analysis techniques. In some embodiments, the acquired calibration data is loaded into the data acquisition and processing system before the start of laser ablation cycles. Depth as a function of the number of incident laser pulses is quantified via calibration using a calibration target with known ablation depth and corresponding number of ablation cycles. The depth calibration data is determined by measuring the amount or thickness of ablated material per laser pulse incident on the target.

The method further includes performing at least one ablation cycle. The ablation cycle includes generating a pulsed optical beam, homogenizing the intensity of the optical beam to produce an optical illumination zone of substantially uniform optical energy on a surface of the target, and delivering the optical beam on the surface of the coating to generate an ablation plasma.

The method further includes generating time resolved spectral data by detecting the emission signals using a time resolved spectral detection system. Time-resolved spectral analysis of the emission signals emitted from the plasma is achieved using a combination of a spectrometer and a gated photodetector, delayed with respect to initiation of the plasma. Absolute elemental concentration is determined in near real-time using the time resolved spectral data and the predetermined calibration data. In a non-limiting example, the absolute elemental concentration is determined by correlating the LPS signals to the known concentrations using regression analysis.

In certain embodiments, a plurality of data acquisition cycles is used to determine elemental concentration. In some embodiments, tens of thousands of successive spectra are typically accumulated during a single target analysis. In one embodiment, analysis and elemental concentration determination as a function of depth is accomplished by programming software instructions, for example, using LabView™ software. In some embodiments, the spectral data collected may be displayed on a computer screen and/or saved for future display and analysis.

In certain embodiments, a plurality of ablation cycles through a desired thickness of the target is performed to determine elemental concentration in successively ablated target depths. In some embodiments spectral data from two or more successive ablation cycles is combined to generate elemental concentration at a desired resolution.

In one embodiment, the emission spectrum for a particular element is selected and plotted as a function of the depth in the target. The number of laser pulses used in the ablation of the target is first correlated to ablation depth using depth calibration data, resulting in a depth profile of the target for the particular element. In embodiments where depth profiling of coatings is performed, to prevent damage to the underlying substrate, ablation of the target is stopped and data acquisition is concluded on determination of a predetermined level of increase or decrease in the elemental concentration of an element present or absent in the coating but not present or absent respectively in the substrate. In some embodiments, conclusion of data acquisition is achieved manually, for example by shuttering the laser, while in other embodiments it is automated, for example, instruction is sent to the laser to stop lasing or a shutter is automatically activated to stop the beam reaching the target.

As will be appreciated by those skilled in the art, the embodiments and applications illustrated and described above may include or be performed by appropriate executable code in a programmed computer. Such programming will comprise a listing of executable instructions for implementing logical functions. The listing can be embodied in any computer-readable medium for use by or in connection with a computer-based system that can retrieve, process and execute the instructions.

In the context of embodiments of the present invention, the computer-readable medium is any means that can contain, store, communicate, propagate, transmit or transport the instructions. The computer readable medium can be an electronic, a magnetic, an optical, an electromagnetic, or an infrared system, apparatus, or device. An illustrative, but non-exhaustive list of computer-readable media can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical). Note that the computer readable medium may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

In one embodiment of the present invention, the computer-readable medium may store instructions for instructing a data acquisition and processing system for initiating a data acquisition cycle and recording time-resolved spectral data. The computer-readable medium may further include calibration data and include instructions for calculating elemental concentration depth profile using the time-resolved spectral data and calibration data. The computer readable medium may include instructions to display the elemental concentration as a function of coating depth.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

EXAMPLES

Figure 6:
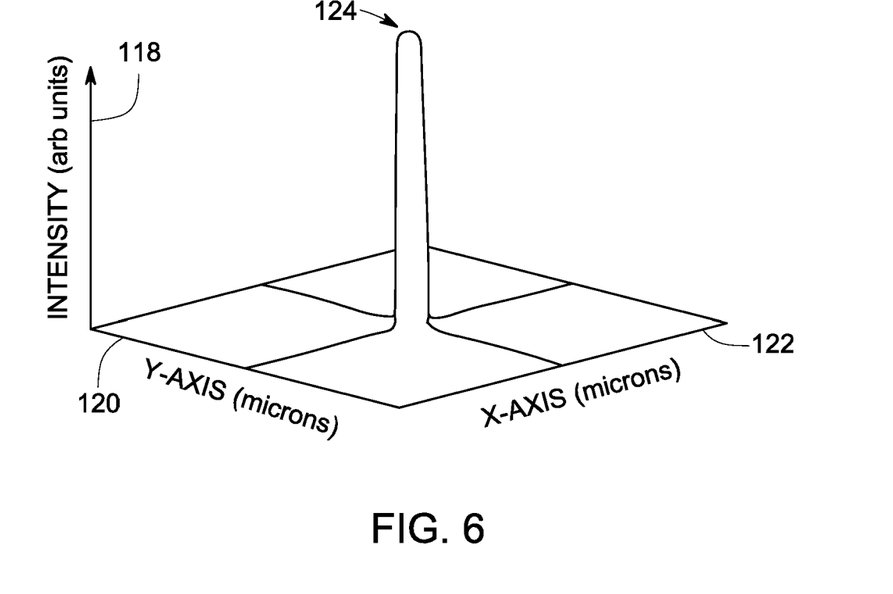
FIG. 6 is a graphical representation of a 3-D intensity profile of a laser beam in one embodiment of the present invention.
Figure 7:
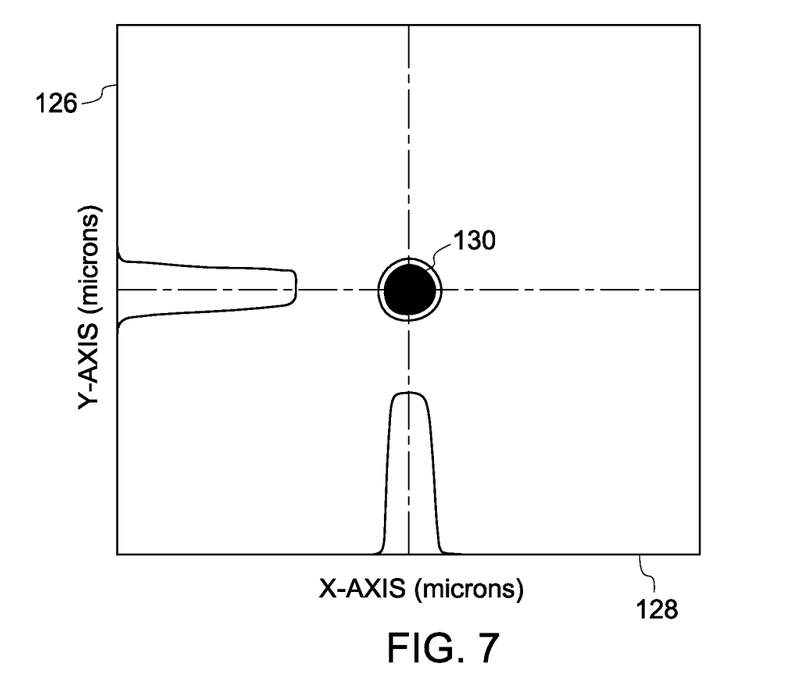
FIG. 7 is a graphical representation of a 2-D intensity profile of a laser beam in one embodiment of the present invention.

A "free space" optical probe system configuration of the laser plasma spectroscopy system as shown in FIG. 2 was built in accordance with one embodiment of the present invention. The system included a Nd:YAG laser configured to emit ~45 mJ laser pulses at a wavelength of 1064 nm at 20 Hz repetition rate. A collimating element including positive and negative lenses was used to generate a collimated beam of about 600 microns in diameter with a flat topped uniform intensity profile. As used herein the term "flat topped uniform intensity profile" refers to an intensity profile capable of producing an optical illumination zone of substantially uniform optical energy for target ablation with one example being shown in FIGS. 6 and 7. FIG. 6 shows the 3 dimensional (3D) profile of the ~45 mJ laser beam pulses at a target surface distance. The 3D plot of the intensity 118 versus the beam spot dimensions along the Y-axis 120 and X-axis 122 shows a substantially flat-topped, uniform intensity profile 124 across the beam spot. FIG. 7 is a 2 dimensional cross-sectional view of the intensity profile with respect to X-axis 126 and Y-axis 128. A uniform intensity distribution is found in the area 130 of the beam profile.

A turbine blade substrate with a Ni/Cr/Al/Y coating was used as a target for elemental concentration depth profile analysis. The coating thickness was about 275 μm. Calibration data for various elements was previously acquired using a sample target with a known elemental concentration depth profile which was received by the data acquisition and processing system. An electron microprobe analysis of the same coating was also performed. The microprobe analysis elemental concentration data was used as control data. A ~45 mJ laser pulse incident on the coating resulted in the creation of an ablation plasma at the target surface. The emission signals from the ablation plasma were observed and the time resolved spectral data were recorded using a time resolved spectral detection system in combination with a data acquisition and processing system. At every laser pulse incident on the coating, coating material corresponding to a thickness of few nanometers was ablated and ablation plasma formed. This cycle of coating material ablation followed by detection of the emission signals was repeated throughout the depth of the coating.

Figure 8:
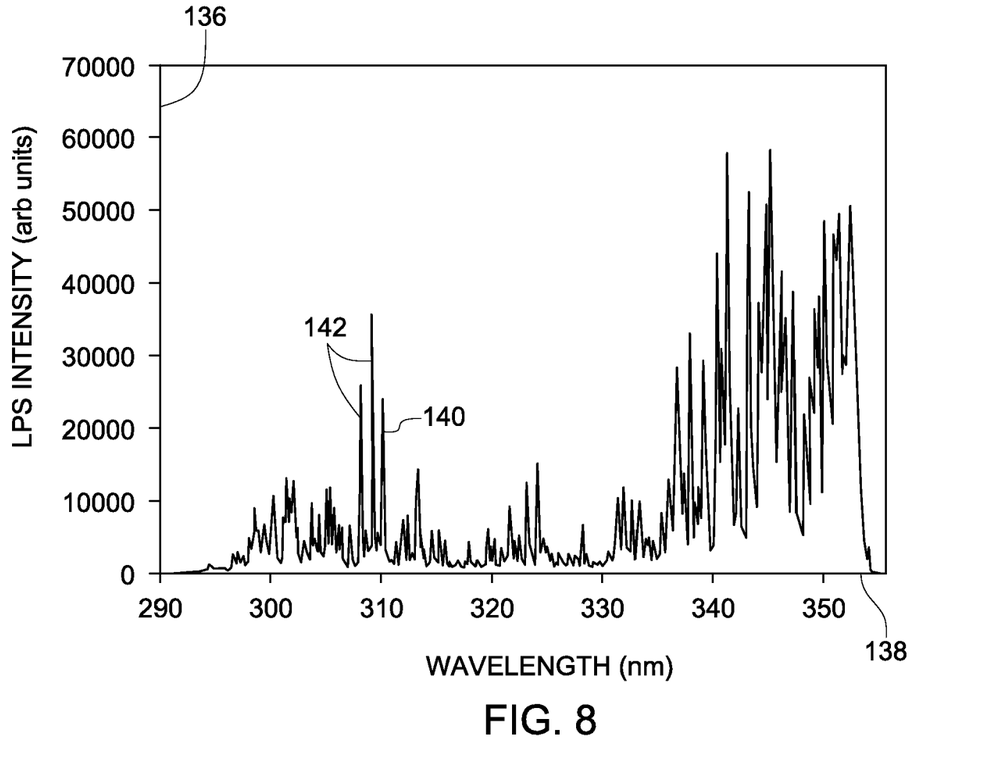
FIG. 8 is a graphical representation of time-resolved spectral intensity versus wavelength measured for a coating using laser plasma spectroscopy in one embodiment of the present invention.

FIG. 8 illustrates time resolved spectral data for the Ni/Cr/Al/Y coating as measured by the laser plasma spectroscopy system. In FIG. 8, the Y axis 136 represents the time resolved spectral intensity obtained from laser plasma spectroscopy of the coating, and the X-axis 138 represents the emission wavelengths of the ablation plasma. Each peak corresponds to a different element present in the coating. Peak 140 corresponds to emission from the element nickel and peaks 142 correspond to emissions from the element aluminum. This spectral intensity data in combination with spectral intensity calibration data is then used to generate elemental concentration depth profile curves.

Figure 9:
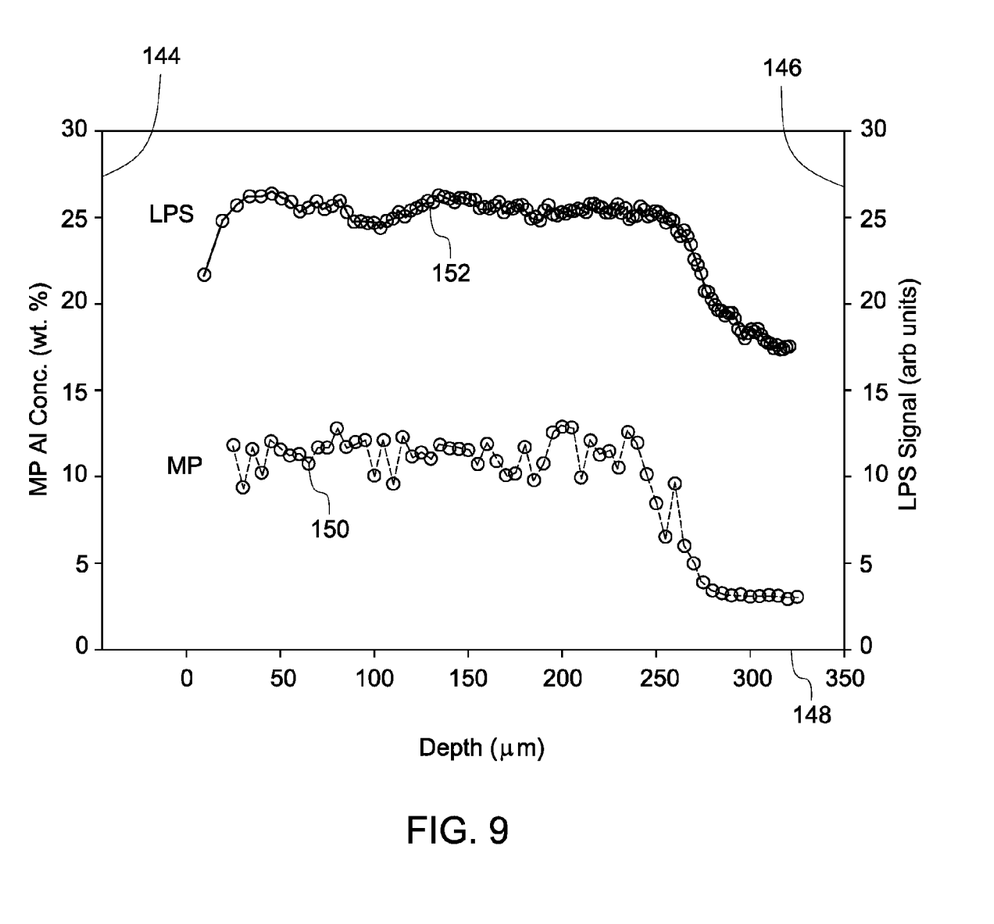
FIG. 9 is a graphical representation of elemental concentration versus measurement depth in a coating using electron microprobe analysis and laser plasma spectroscopy in one embodiment of the present invention.

FIG. 9 illustrates the elemental concentration depth profile curves obtained using electron microprobe (MP) analysis and LPS analysis without calibration in accordance with one embodiment of the present invention. In FIG. 9, the $Y_1$ axis 144 represents the elemental concentration of aluminum in weight % obtained from the microprobe analysis of the same target, the $Y_2$ axis 146 represents the LPS intensity signal in arbitrary units, and the X-axis 148 represents the measurement depth of the coating. The difference between microprobe analysis data 150 and the LPS data without calibration 152 clearly shows the calibration would be beneficial to obtain absolute elemental concentrations.

Figure 10:
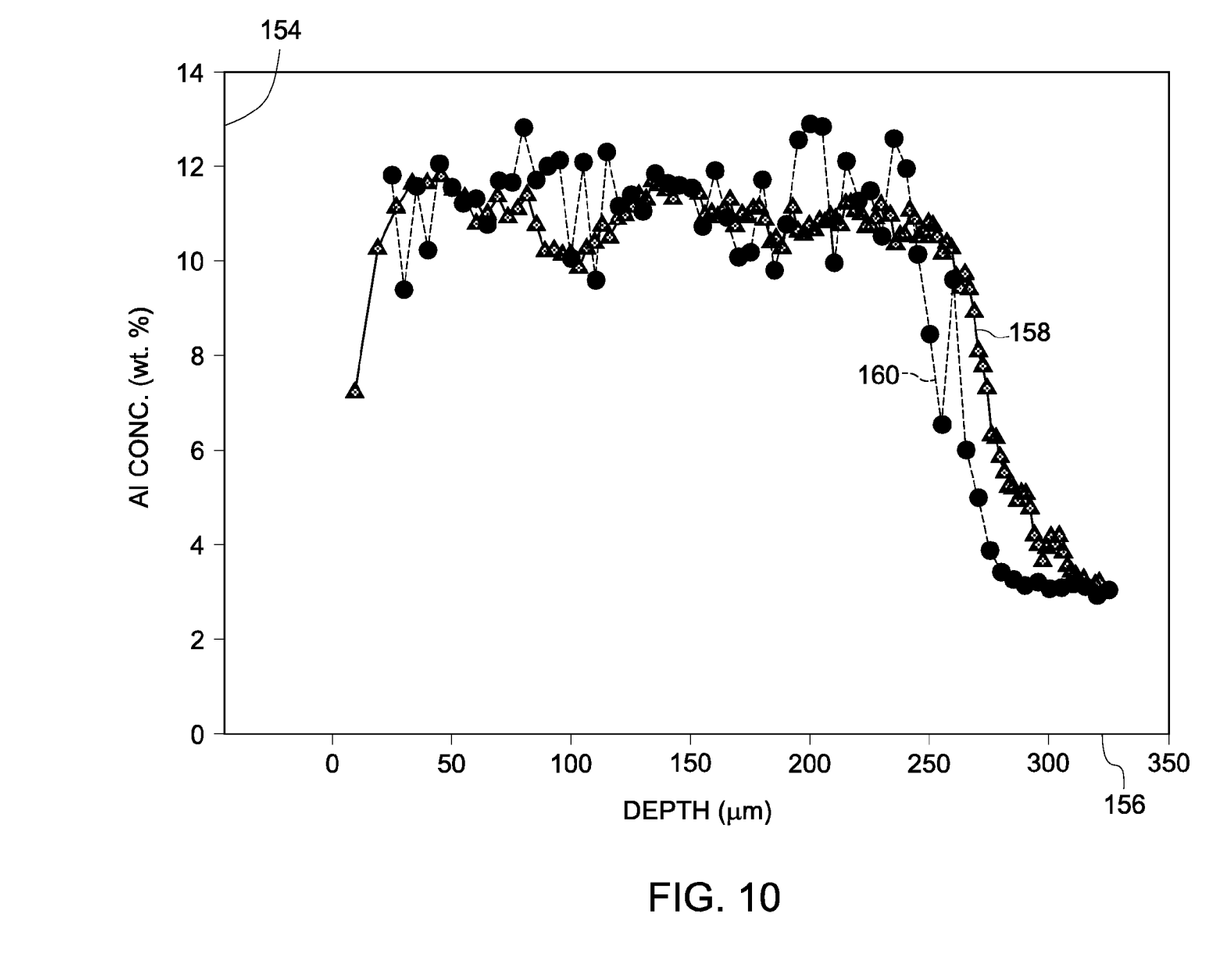
FIG. 10 is a graphical representation of calibrated elemental concentration versus depth in a coating using electron microprobe analysis and laser plasma spectroscopy in one embodiment of the present invention.

As the raw LPS signal is a measure of the intensity of the spectral data, the corresponding elemental concentration data is generated by using the previously determined calibration data. The calibration data provides a measure of the spectral intensity as a function of the elemental concentration for various elements present in the coating. FIG. 10 is a comparative graph of the elemental concentration as determined by the electron microprobe analysis and by the real-time LPS system and method described above in accordance with one embodiment of the present invention. The Y axis 154 represents the elemental concentration of aluminum in weight % obtained from microprobe analysis and LPS and the X-axis 156, the measured depth of the coating. As the previously determined data is already present in the data acquisition and processing system, a near real-time monitoring of the elemental concentration is enabled by the embodiments of the present invention. The microprobe analysis data 158 and the LPS calibrated data 160 show substantially similar profiles indicating that the LPS technique with calibration in accordance with embodiments of the present invention, provides a viable real time monitoring of the depth profile of the elemental concentration.

Figure 11:
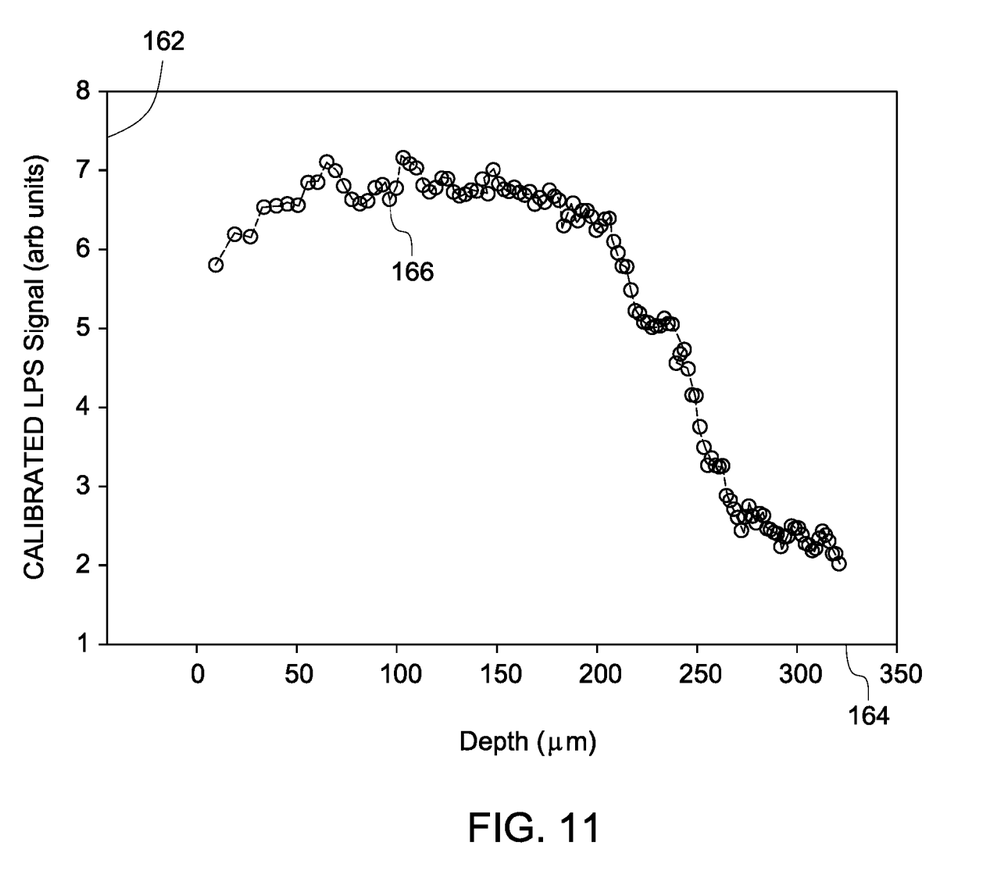
FIG. 11 is a graphical representation of elemental concentration versus depth in a coating in one embodiment of the present invention, used for substrate location identification/damage prevention.

Damage to the substrate was avoided by tracking the depth profile of an element (e.g., Yttrium) that was present in the coating but not in the substrate. By observing the spectra in real time as a depth profile is being obtained, the laser source was turned off as this element began to decrease in the intensity of its emission. FIG. 11 displays the depth profile of Yttrium in the same sample. The Y-axis 162 represents the intensity signal in arbitrary units, and the X-axis 164, the measurement depth of the coating. In this example, the coating thickness was about 275 microns and Yttrium was only present in the coating and not in the substrate. The elemental concentration depth profile 166 is shown in FIG. 11. As can be seen from FIG. 11, the Yttrium concentration starts to decrease at about 200 μm. When the elemental concentration of the Yttrium element fell to below 50% of its initial level the laser was shuttered or turned off.

The optical sensor interrogation system and method described herein have the advantage that targets can be analyzed for elemental concentration as a function of depth in situ and in the field. Expense and time of disassembly of parts or machinery and transport of these parts to an off-site analytical lab and reassembly of machinery is avoided. No sample preparation is required, and only a small quantity of material (on the order of nano-or micrograms) is vaporized and utilized for analysis. Analysis is near real-time, since elemental quantification can be obtained using a single laser shot and previously determined calibration data, and, additionally, depending on the laser parameters, the number of repeated laser shots required to obtain a complete depth profile requires only minutes. As the detection system has wide spectral range, spectral lines corresponding to different elements can be simultaneously identified.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An in-situ laser plasma spectroscopy (LPS) system for automated near real-time elemental depth profiling of a target, comprising:
    an optical source configured to generate an optical beam, wherein the optical beam is pulsed;
    an optical probe system configured to deliver the optical beam from the optical source to a surface of a target to generate an ablation plasma;
    a time resolved spectral detection system configured to generate time resolved spectral data from emission signals from the ablation plasma; and
    a data acquisition and processing system configured to acquire the time resolved spectral data to determine, in combination with predetermined calibration data, an absolute elemental concentration of the target as a function of depth in near real-time.

2. The system of claim 1, wherein the optical probe system is configured to deliver the optical beam the surface of a target comprising a coating on a substrate.

3. The system of claim 1, wherein the optical probe system comprises a beam-shaping element configured to control one or more beam parameters.

4. The system of claim 3, wherein the beam-shaping element comprises an intensity-homogenizing element to produce an optical illumination zone of substantially uniform optical energy on the surface of the target.

5. The system of claim 4, wherein the intensity-homogenizing element is at least one device selected from the group consisting of spatial filters, mode scramblers, non-linear attenuators, and combinations thereof.

6. The system of claim 3, wherein the beam-shaping element is a beam collimating element.

7. The system of claim 6, wherein the collimating element comprises a positive lens and negative lens combination.

8. The system of claim 1, wherein the optical probe system comprises a spectral separation element to spatially separate emission signals from the path of the optical beam.

9. The system of claim 1, wherein the optical probe system comprises an optical pulse delivery fiber configured to deliver the optical beam to the surface of the target.

10. The system of claim 9, wherein the optical pulse delivery fiber is further configured to collect the emission signals from the plasma.

11. The system of claim 9, wherein the optical probe system further comprises a probe head coupled to the optical pulse delivery fiber, the probe head comprising a probe lens configured to focus and direct the optical beam at surface of the target.

12. The system of claim 11, wherein the optical probe system further comprises an alignment fixture for aligning the probe head to direct the optical beam substantially normal to the surface of the target.

13. The system of claim 12, wherein the alignment fixture comprises a sheath encasing at least part of the optical pulse delivery fiber and the probe lens, wherein the sheath extends beyond the probe lens by a length substantially equal to a focal length of the probe lens.

14. The system of claim 11, wherein the optical probe system further comprises a probe head position controller to dynamically adjust the probe head distance from the surface of the target.

15. The system of claim 1, wherein the optical probe system comprises a configuration for sub-volume sampling of the ablation plasma.

16. The system of claim 1, wherein the optical probe system comprises off-axially positioned emission signal delivery fiber.

17. The system of claim 1, wherein the optical source comprises a pulsed laser source.

18. The system of claim 16, wherein the optical source comprises a Nd:YAG laser, wherein the optical beam comprises a fundamental or a harmonic of Nd:YAG laser output.

19. The system of claim 1, wherein the time resolved spectral detection system comprises a spectrometer and a photodetector.

20. The system of claim 19, wherein the photodetector is at least one device selected from the group consisting of a photo-diode array, a charge coupled device, an intensified charge-coupled device, a gated charge coupled device, an array of individually positioned photomultipliers, and combinations thereof.

21. The system of claim 19, further comprising a photodetector controller configured to time-gate and delay photodetector activation to generate the time resolved spectral data.

22. The system of claim 1, wherein the data acquisition and processing system is configured to receive calibration data from a computer readable medium.

23. The system of claim 1, wherein the data acquisition and processing system comprises a portable computing device for performing near real-time analysis.

24. The system of claim 1, wherein two or more elements of the system are removably coupled together.

25. The system of claim 1, wherein the target is a component of a turbine system.

26. An in-situ, portable laser plasma spectroscopy system for automated near real-time elemental depth profiling of a coating, comprising:

an optical source configured to generate an optical beam, wherein the optical beam is pulsed;

an optical probe system configured to deliver the optical beam from the optical source to a surface of a coating on a substrate to generate an ablation plasma, wherein the optical probe system comprises a beam-shaping element to produce an optical illumination zone of substantially uniform optical energy through a thickness of the coating;

a time resolved spectral detection system configured to generate time resolved spectral data from emission signals from the ablation plasma; and a data acquisition and processing system configured to acquire the time resolved spectral data to determine, in combination with predetermined calibration data, an absolute elemental concentration of the coating as a function of depth in near real-time.

27. The system of claim 26, wherein the data acquisition and processing system is configured to stop ablation of the target on determination of a predetermined level of increase or decrease in elemental concentration of an element present or absent in the coating or substrate.

28. A method for in-situ, near real time depth profiling, comprising:

(a) acquiring calibration data;

(b) performing at least one ablation cycle comprising:
generating an optical beam, wherein the optical beam is pulsed;
collimating the optical beam to produce uniform ablation in successive ablation cycles;
homogenizing the intensity of the optical beam to produce an optical illumination zone of substantially uniform optical energy on a surface of the target; and
delivering the optical beam at the surface of the coating to generate an ablation plasma;

(c) generating time resolved spectral data from emission signals received from the ablation plasma; and (d) using the time resolved spectral data and the calibration data for determining absolute elemental concentration at the probed surface of the target in near real-time.

29. The method of claim 28, wherein the calibration data comprises elemental spectral intensity calibration data and depth calibration data.

30. The method of claim 29, wherein acquiring elemental spectral intensity calibration data comprises determining elemental spectral intensity for a given concentration using a calibration target with a known elemental concentration using electron microprobe analysis.

31. The method of claim 29, wherein acquiring depth calibration data comprises determining ablation depth per incident pulse of the optical beam using a calibration target with known ablation depth and corresponding number of ablation cycles.

32. The method of claim 28, comprising performing a plurality of ablation cycles and combining spectral data from two or more successive ablation cycles to generate elemental concentration at a desired resolution.

33. The method of claim 28, comprising repeating steps (a) to (d) to determine elemental concentration in successively ablated surfaces of the target.

34. The method of claim 28, wherein the target comprises a coating on a substrate.

35. The method of claim 34, further comprising monitoring the elemental concentration of an element present or absent in the coating or substrate.

36. The method of claim 35, further comprising stopping ablation of the target and concluding data acquisition on determination of a predetermined level of increase or decrease in the elemental concentration of an element present or absent in the coating or substrate, to prevent damage to the substrate.

37. A method for in-situ, near real time depth profiling, comprising:
 (a) acquiring calibration data;
 (b) performing at least one ablation cycle comprising:
  generating an optical beam, wherein the optical beam is pulsed;
  homogenizing the intensity of the optical beam to produce an optical illumination zone of substantially uniform optical energy on a surface of the target; and
  delivering the optical beam at the surface of the coating to generate an ablation plasma;
 (c) generating time resolved spectral data from emission signals received from the ablation plasma;
 (d) using the time resolved spectral data and the calibration data for determining absolute elemental concentration at the probed surface of the target in near real-time; and
 (e) dynamically adjusting a distance between a probe-head delivering the optical beam to the surface of the target and the surface of the target for successive ablation cycles.

* * * * *